United States Patent [19]

Valin

[11] 4,064,874
[45] Dec. 27, 1977

[54] PROTECTIVE ORTHOPEDIC DEVICE

[76] Inventor: Norman A. Valin, 4803 N. Crescent Ave., Norridge, Ill. 60656

[21] Appl. No.: 689,595

[22] Filed: May 24, 1976

[51] Int. Cl.² .............................................. A61F 3/00
[52] U.S. Cl. ...................................... 128/80 C; 2/22
[58] Field of Search ................ 128/80 C, 80 R, 80 F, 128/88, 165, 87 R; 2/22, 24

[56] References Cited

U.S. PATENT DOCUMENTS

| | | | |
|---|---|---|---|
| 1,092,836 | 4/1914 | Hart | 128/80 C |
| 1,622,211 | 3/1927 | Sheehan | 2/22 |
| 2,195,024 | 3/1940 | Bullock | 128/88 |
| 2,959,168 | 11/1960 | Shook | 128/80 F |
| 3,194,233 | 7/1965 | Peckham | 128/80 C |
| 3,786,804 | 1/1974 | Lewis | 128/80 C |

*Primary Examiner*—John D. Yasko
*Attorney, Agent, or Firm*—Neuman, Williams, Anderson & Olson

[57] ABSTRACT

An elastic orthopedic device for protecting, for example, the knee joint, has metallic inserts which are articulated for full forward and rearward motion yet which resist lateral forces applied to the joint and tendencies of the joint to dislocate in a lateral direction.

6 Claims, 8 Drawing Figures

PROTECTIVE ORTHOPEDIC DEVICE

This invention relates generally to orthopedic support devices and more particularly to an elastic support having articulated lateral supports inserted therein.

The knee is the largest joint of the body and must support the entire weight of the upper body during the normal course of walking or running. Injuries to the knee are serious, due not only to the fact that the knee plays a major part in the normal human gait but, since the knee must support great stresses, such stresses may aggravate any injury and prolong the healing process, unless the injured person can keep all weight off the knee as, for example, by using crutches or remaining in traction until healing is completed.

Some activities place greater stresses on the knee than others, as for example the types of stresses experienced in athletic participation and competition. Such stresses may produce no problems for a sound knee; however, any injury producing a lasting residual result may leave the injured person with a chronic condition in which the knee, when placed under large or unusual stresses, may dislocate or "lock". Such a condition generally requires use, by the injured person, of some type of supportive device during those times that the person anticipates the knee will be placed under unusual stresses. Common examples are the supportive devices worn by basketball players and skiers to prevent the knee from dislocating while at the same time assuring, to as great a degree as possible, a full range of flexibility and mobility of the knee joint. Such supportive devices may also be of use while recovering from knee injuries during which support and protection of the knee joint aids in proper and correct healing.

Previous supportive devices have made extensive use of heavy duty elastic material to provide support for the knee and to reduce swelling while attempting to permit full articulation of the knee joint. Such devices, however, furnish little or no effective lateral protection or support. Other appliances may feature pivotally hinged external metallic frameworks attached at their free end to bands or cuffs which may be strapped or buckled above and below the knee. While such divices may provide some degree of lateral support and may reduce the amount of force exerted on the knee during walking motions, such devices have generally been uncomfortable, unsightly and next to impossible to wear under clothing. Thus the need exists for an improved knee support device which provides full lateral support in a compact and comfortable configuration.

Accordingly, this invention has the following objects:

To provide orthopedic devices which supply lateral support to a joint of the body;

To provide such devices in forms which are comfortable to wear and which do not hamper normal joint articulation;

To provide such devices in forms streamlined enough to be worn under clothing;

To provide such devices in forms relatively inexpensive to manufacture and convenient to apply; and To provide such devices in forms sized to accommodate a wide range of limb sizes and configurations.

These and further objects will become more apparent upon consideration of the accompanying drawings in which.

Figure 1:
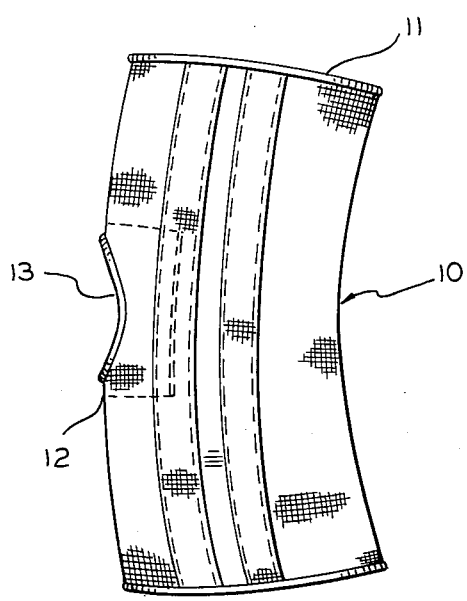
FIG. 1 is a side elevation of the orthopedic device of the subject invention.

Consistent with the foregoing objects, applicant herein provides a protective orthopedic device for joints of the body, with tubular elastic support means 11 having axially peripherally extending sleeve means 14 and 16 formed therein. Stay 15 is inserted in channel 14 and articulated brace member 17 is inserted in channel 16 whereby said orthopedic device articulates fully in the normal direction of articulation of the joint, yet which resists forces lateral to said direction, as exemplified by Force F.

Referring now to FIG. 1, the numeral 10 indicates generally a knee support device which, in this embodiment, includes a somewhat tubular elastic support 11 having inner support pads 12 and patellar opening 13.

Figure 2:
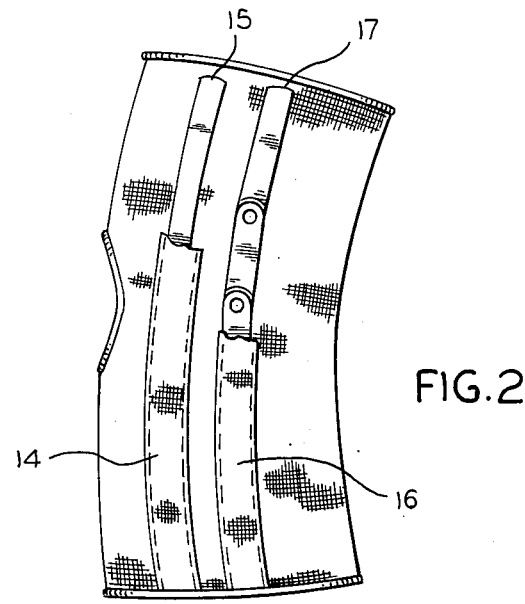
FIG. 2 is side elevation of the device in FIG. 1 with the side channels partially broken away to expose the stay and the articulated brace member.
Figure 3:
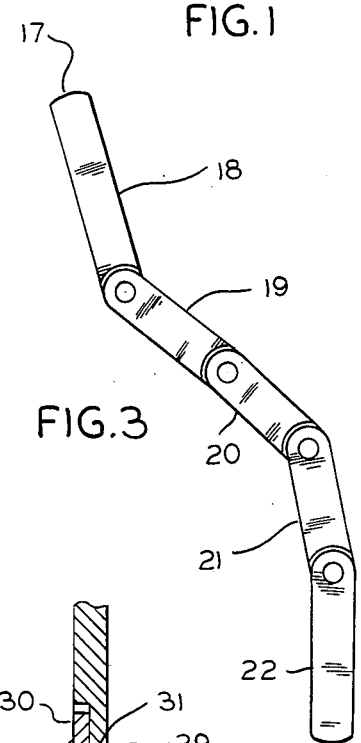
FIG. 3 is a side elevation of the brace member in an articulated attitude.
Figure 8:
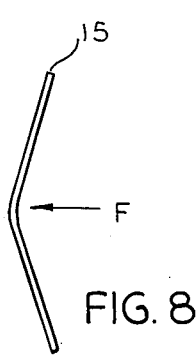
FIG. 8 is a front view illustrating the effect of force F on the stay of FIG. 2.

Tube 11 has stitched along each of its sides stay channels 14 into which are inserted spring steel members 15, and brace channels 16 into which are inserted articulated brace members 17, as illustrated in FIG. 2. Such tubular elastic support members are well known in the art, however, heretofore such support members have utilized only spring steel inserts whose primary function has been to enable the supportive device to maintain its original shape in much the same manner as a collar stay maintains the shape of a collar. Minimal lateral support is offered by such spring steel inserts as may be seen illustrated in FIG. 8 which shows that only a relatively small force F is required to deform such spring steel inserts considerably in a lateral direction.

The present invention, however, features an articulated insert 17 comprising, in this embodiment, links 18, 19, 20, 21 and 22. Such links are joined at pivot points 23, 24, 25 and 26 and are secured by flathead rivets 27.

Figure 5:
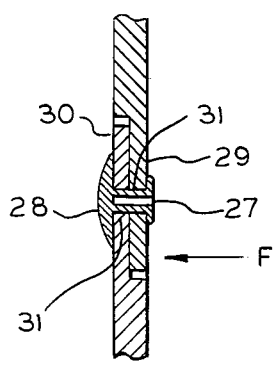
FIG. 5 is a view along 5—5 of FIG. 4.
Figure 4:
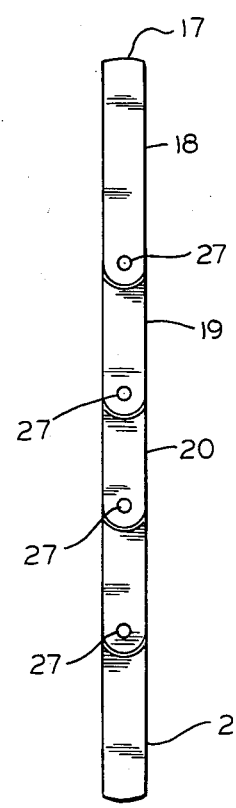
FIG. 4 is a side elevation of the member of FIG. 3 illustrating the relative proportions of the individual links.

As illustrated in Fig. 5, a typical link joint 28 includes matching mating tongue portions 29 and 30 of adjacent links, through which aligned apertures 31 are formed. Flathead rivet 27 is then inserted through the aligned apertures to pivotally secure said adjacent links together. Such joints allow full articulation in a plane perpendicular to the axis of the joint while at the same time rigidly resisting any force exerted perpendicular to said plane of articulation. If for example, force F is applied to joint 28, tongue 30 will be forced against tongue 31 which, with rivet 27 will prevent any further lateral displacement. The mating surfaces of tongues 30 and 31 may be highly polished or treated with an anti-friction compound to assure full articulation even while any such lateral force may be applied to the device.

Thus constructed, the articulated brace will not only prevent lateral forces from stressing the knee joint but will also tend to prevent or limit any lateral movement of the femoral portion with respect to the tibial portion of the knee as may result, for example, from any injury weakening or destroying any of the complex major tendons or ligaments which hold the knee together.

To achieve effective support while allowing free articulation of the knee joint, the individual segments of brace members 17 must be carefully proportioned. One such set of proportioned links found experimentally to operate successfully features the longest link 18 positioned furthest above the knee. Links 19 and 21 are of equal length and are joined to both ends of central link 20 which is the shortest of the five links. Lowermost link 22, fastened to the other end of link 21, is longer than any of the intermediate links yet shorter than link 18. As presently conceived, link 18 is 3-1/16 inches long; links 19 and 21 are 2-5/16 inches; link 20 is 2-1/16 inches; and link 22 is 2-9/16 inches. Various sizes and size ratios may be determined with regard to the height and weight of the individual user, and with regard to the joint with which the device is to be used.

Figure 6:
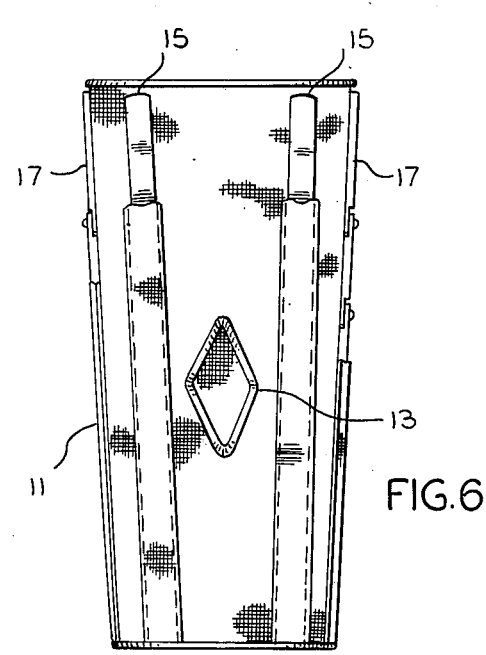
FIG. 6 is a front elevation of the device of FIG. 1 illustrating the positioning of the articulated brace members.
Figure 7:
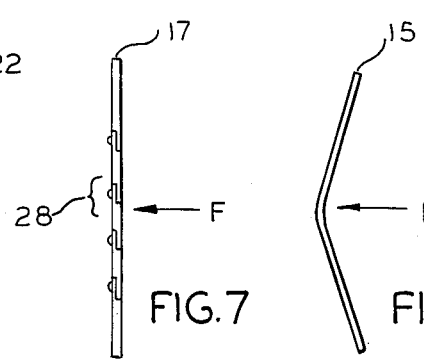
FIG. 7 is a front view of the brace member of FIG. 3 with lateral force F applied thereto.

As illustrated in FIGS. 2 and 6, articulated brace members 17 are inserted into brace channels 16 and are oriented laterally on either side of the knee. Substantially normal knee articulation is then possible during the healing period.

Although in the above embodiment, the present invention has been discussed as a protective knee device, it is felt that such a device properly proportioned and constructed would serve, for example, as an elbow protector as well.

While the foregoing has described a specific embodiment of the invention, it is to be understood that this embodiment is presented by way of example only and is not intended to limit the scope of the invention. It is anticipated that others skilled in the art will perceive variations which, while differing from the foregoing embodiment, do not depart from the spirit and scope of the invention.

I claim:

1. A compact protective orthopedic device for joints of the body, said device comprising: tubular elastic support means, said support means being adapted to substantially surround one of said joints, said support means having formed axially and peripherally therein sleeve means; and brace means being shaped and dimensioned to be insertingly accommodated by said sleeve means and said brace means being characterized as fully articulated in the normal direction of articulation of said joint, said brace means being further characterized as being rigid in a direction transverse to said normal direction, said bracing means including more than two link members, each said link member being greater longitudinally than laterally and being pivotally articulated to its adjacent partners for flexing in a common plane and each said brace means having more than one pivot for permitting said link members to pivotally articulate with respect to one another and with said joint.

2. The device as recited in claim 1 wherein each said link member overlaps its immediately adjacent partners at said pivotal attachments.

3. The apparatus as recited in claim 1 wherein said brace means includes five links.

4. The apparatus as recited in claim 3 wherein said links are proportioned in the ratios of 1.5: 1.1: 1: 1.1: 1.25.

5. A compact protective orthopedic device for a joint of the body, said device comprising: generally tubular elastic support means, said support means having formed axially peripherally therein sleeve means; and brace means, said brace means including more than two articulated link members, said link members having axially elongated links and a plurality of pivots therebetween and being adapted to articulate in a single common plane while rigidly resisting forces transverse to said plane, said brace means shaped and dimensioned to be insertingly accommodated by said sleeve means, said brace means being oriented to articulate in the normal direction of articulation of said joint, whereby forces exerted transverse to said normal direction are rigidly resisted by said brace means.

6. A compact protective orthopedic device for joints of the body, said device comprising: a tubular elastic support means, said support means being attached to substantially surround one of said joints having formed axially and peripherally therein sleeve means, brace means being shaped and dimensioned to be insertingly accommodated by said sleeve means and characterized as fully articulated in the normal direction of articulation of the body joint, said brace means being further characterized as being rigid in a direction transverse to said normal direction and including five link members, each said link member being substantially thinner than long and being pivotally articulated to and overlapping its immediate adjacent link member for flexing in a common plane, and said links are proportioned in ratios of 1.5:1.1:1:1.1:1.25.

* * * * *

UNITED STATES PATENT AND TRADEMARK OFFICE
CERTIFICATE OF CORRECTION

PATENT NO. : 4,064,874
DATED : December 27, 1977
INVENTOR(S) : Norman A. Valin

It is certified that error appears in the above—identified patent and that said Letters Patent are hereby corrected as shown below:

Under "References Cited U.S. Patent Documents", insert:

--3,885,252   5/1975   Nakajima    128/80Fx
  2,362,383   11/1944  Lendinara   128/80F--

Signed and Sealed this

Sixth Day of June 1978

[SEAL]

Attest:

RUTH C. MASON
*Attesting Officer*

DONALD W. BANNER
*Commissioner of Patents and Trademarks*